United States Patent
Yuasa et al.

(10) Patent No.: US 11,576,647 B2
(45) Date of Patent: Feb. 14, 2023

(54) APPARATUS AND METHOD FOR PERFORMING INTERVENTIONAL ENDOSCOPIC ULTRASOUND PROCEDURE

(71) Applicant: OLYMPUS CORPORATION, Hachioji (JP)

(72) Inventors: Masaru Yuasa, Allentown, PA (US); Yoshisane Nakamura, Allentown, PA (US); Robert H. Hawes, Orlando, FL (US); Emer M Feerick, Tuam (IE); Damian Muldoon, Loughrea (IE); Rory O'Brien, Clonmel (IE)

(73) Assignee: OLYMPUS CORPORATION, Tokyo (JP)

( * ) Notice: Subject to any disclaimer, the term of this patent is extended or adjusted under 35 U.S.C. 154(b) by 621 days.

(21) Appl. No.: 16/588,070

(22) Filed: Sep. 30, 2019

(65) Prior Publication Data

US 2021/0093288 A1    Apr. 1, 2021

(51) Int. Cl.
*A61B 17/00*    (2006.01)
*A61B 8/08*    (2006.01)
(Continued)

(52) U.S. Cl.
CPC .............. *A61B 8/0841* (2013.01); *A61B 8/12* (2013.01); *A61M 25/10* (2013.01); *A61M 29/02* (2013.01);
(Continued)

(58) Field of Classification Search
CPC ................ A61B 17/3478; A61B 17/34; A61B 2017/0034; A61B 2090/378; A61B 8/12;
(Continued)

(56) References Cited

U.S. PATENT DOCUMENTS 8,317,771 B2    11/2012  Mitelberg et al.
8,328,837 B2 *  12/2012  Binmoeller ......... A61M 25/104
                                                        604/164.01
(Continued)

FOREIGN PATENT DOCUMENTS

EP         2397097 A1    12/2012
EP         2662107 A2    11/2013
WO      2011/056848 A1    5/2011

OTHER PUBLICATIONS

Nov. 4, 2020 International Search Report issued in International Patent Application No. PCT/IB2020/000657.
(Continued)

*Primary Examiner* — Deanna K Hall
(74) *Attorney, Agent, or Firm* — Oliff PLC

(57) ABSTRACT

An apparatus for insertion into a body through a working channel of an endoscope includes a catheter including a dilator, a guide tube disposed in a lumen of the catheter, and a handle including a puncturing actuator operatively coupled to the proximal end of the guide tube. The dilator may be a cautery device and/or a balloon. The apparatus may also include a stylet needle that includes a cutting distal end for puncturing tissue and extends through a lumen in the guide tube. The handle may further include a stopper detachably coupled to the puncturing actuator to fix a position of the puncturing actuator on the handle, and moveable on the handle independently of the puncturing actuator when detached from the puncturing actuator. The disclosed embodiments also include a method for forming a passageway in a wall of a hollow body organ using the apparatus.

10 Claims, 15 Drawing Sheets

(51) Int. Cl.
  *A61B 8/12*    (2006.01)
  *A61M 25/10*   (2013.01)
  *A61M 29/02*   (2006.01)
  *A61B 90/00*   (2016.01)

(52) U.S. Cl.
  CPC .. *A61B 2090/378* (2016.02); *A61M 2029/025* (2013.01)

(58) Field of Classification Search
  CPC . A61M 2029/025; A61M 25/10; A61M 29/02
  See application file for complete search history.

(56) References Cited

U.S. PATENT DOCUMENTS

| | | |
|---|---|---|
| 8,617,196 B2 | 12/2013 | Binmoeller |
| 2013/0090654 A1 | 4/2013 | Clancy |
| 2016/0361088 A1* | 12/2016 | Maguire ............ A61B 17/3415 |

OTHER PUBLICATIONS

Nov. 4, 2020 Written Opinion of the International Searching Authority issued in International Patent Application No. PCT/IB2020/000657.

\* cited by examiner

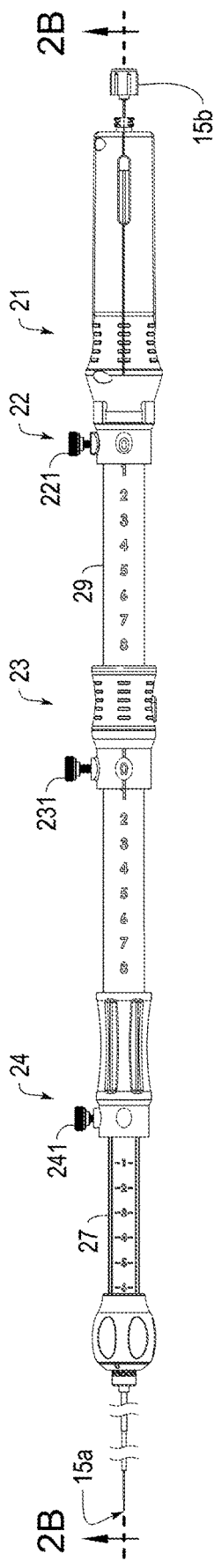
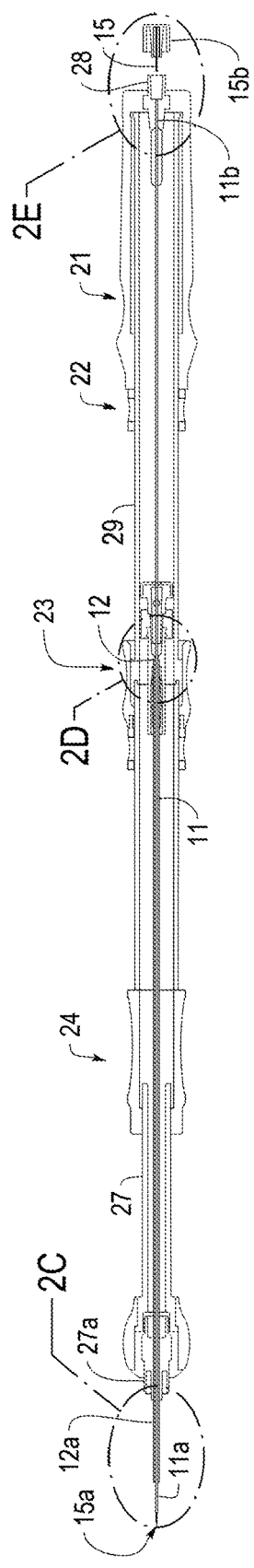
FIG. 2A
FIG. 2B

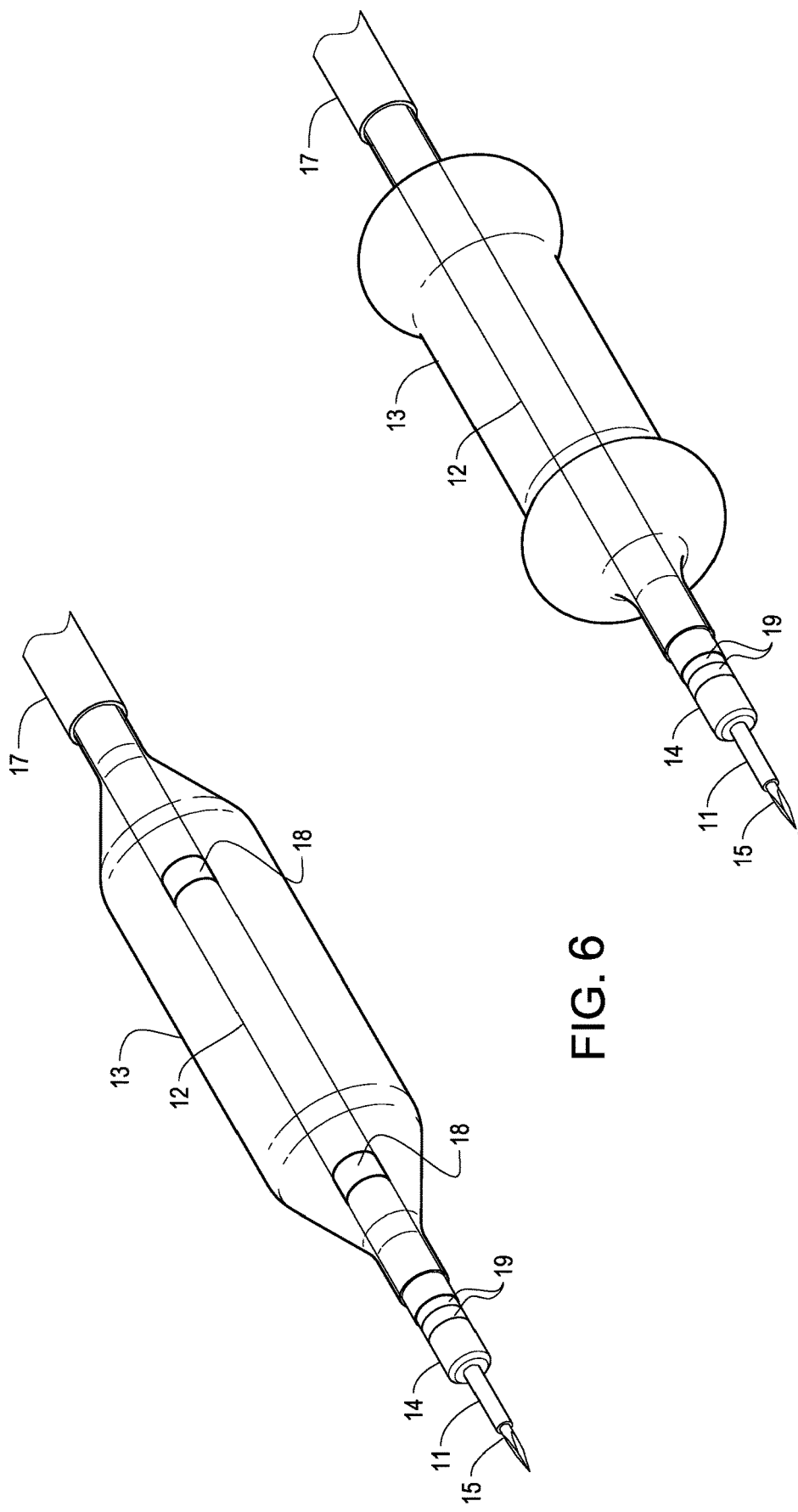

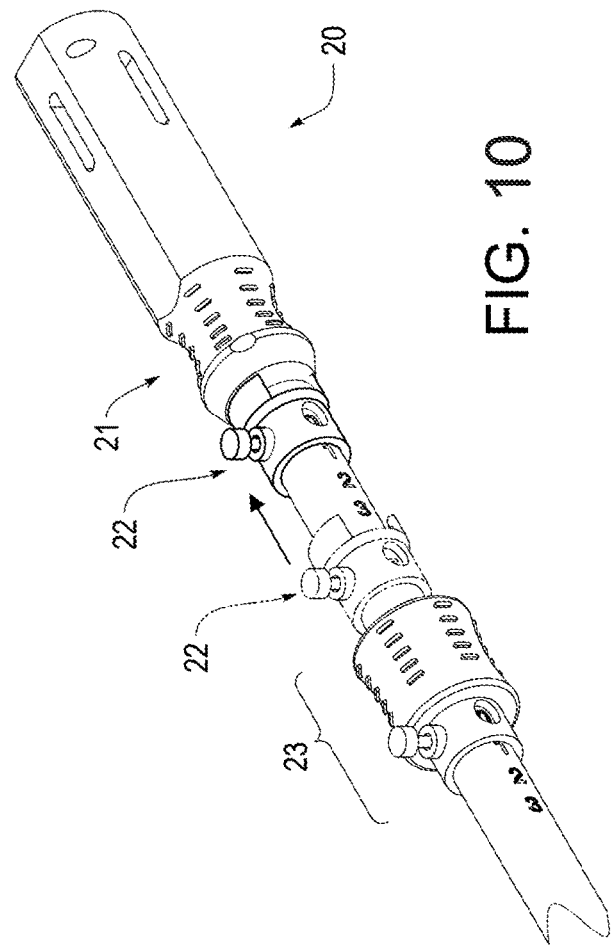
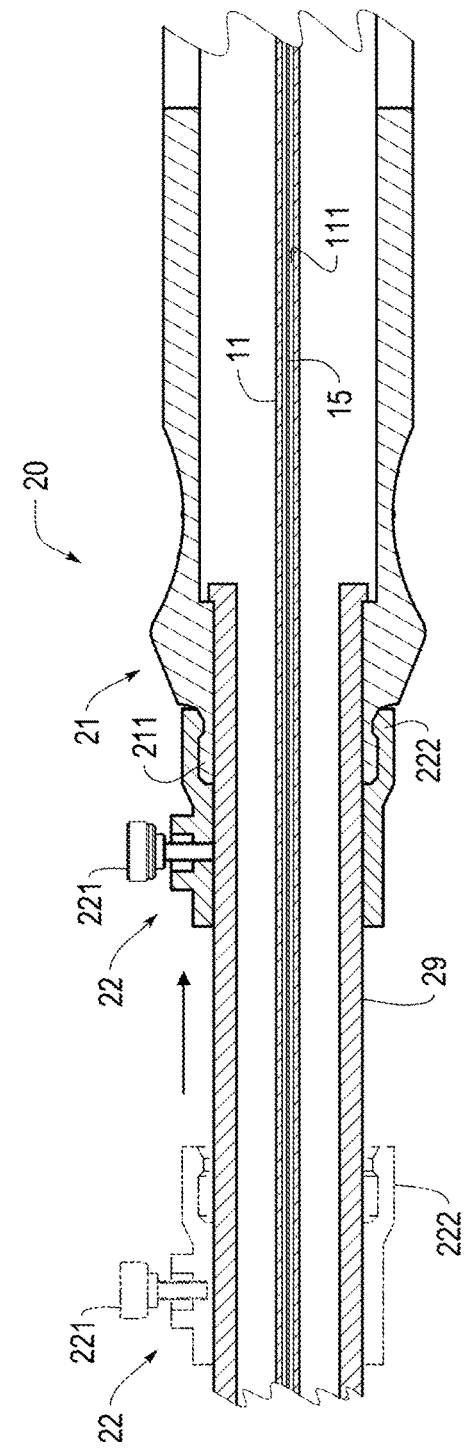

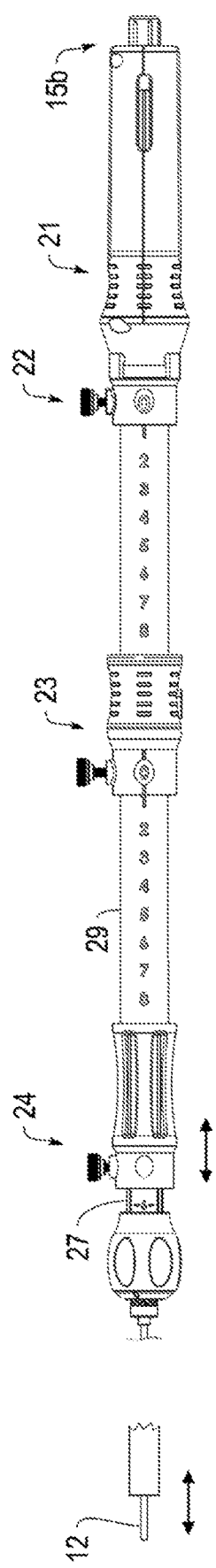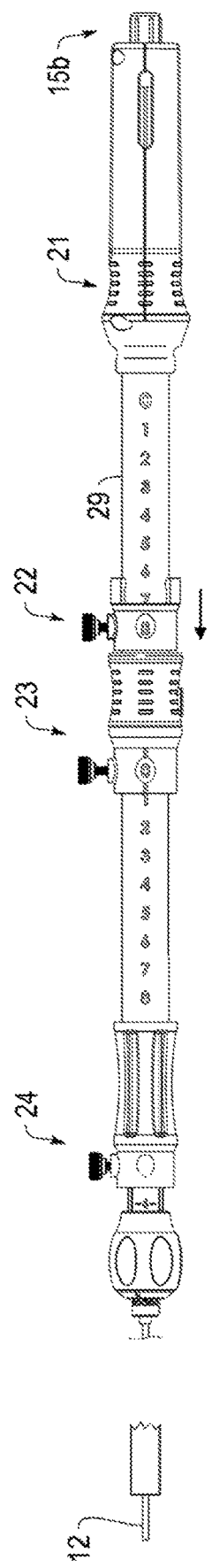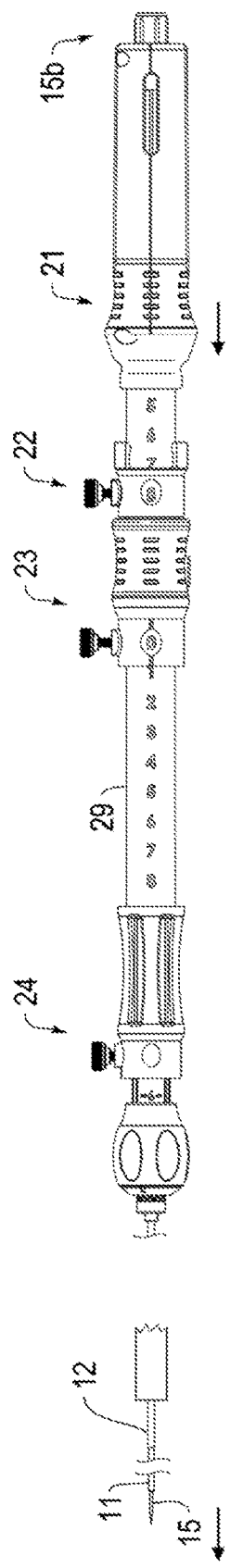
FIG. 13A
FIG. 13B
FIG. 13C

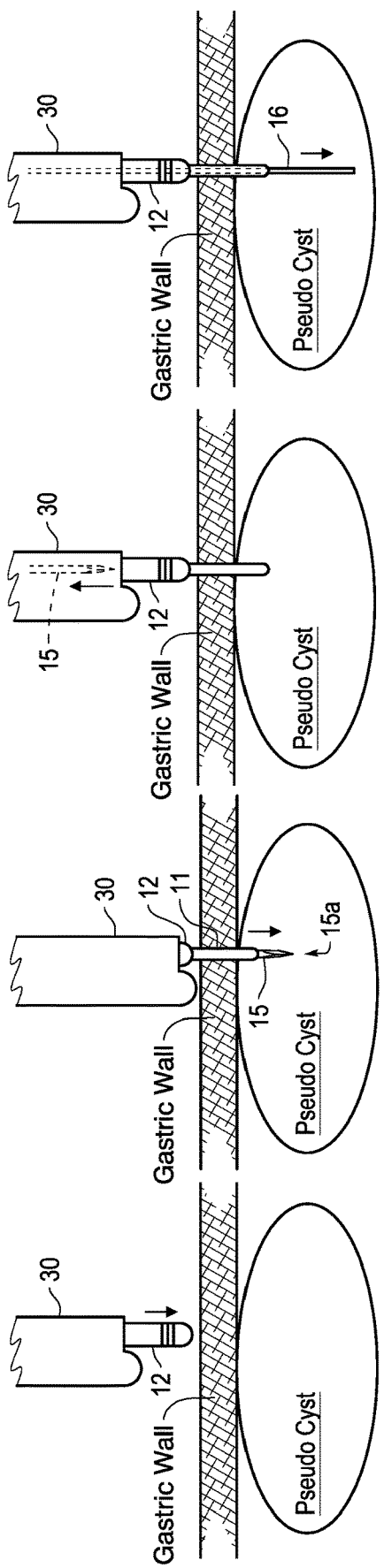

APPARATUS AND METHOD FOR PERFORMING INTERVENTIONAL ENDOSCOPIC ULTRASOUND PROCEDURE

BACKGROUND

Endoscopic Ultrasound (EUS) procedure is a minimally invasive procedure that provides access to organs, lesions, cysts, pseudo cysts, and abscesses in proximity to the gastrointestinal tract for diagnostic and therapeutic purposes. Interventional EUS is often used in pancreatic fluid collection drainage, biliary and pancreatic duct drainage, drainage of the gallbladder, and other conditions, including cases of failed endoscopic retrograde cholangiopancreatography.

But EUS involves multiple steps and instruments. For instance, EUS typically involves advancing one or more puncturing and/or dilation devices through a working channel of an ultrasound endoscope to puncture the target tissue and dilate the punctured passageway to provide a path of access for introduction of a drainage or other device. EUS is a lengthy and cumbersome procedure involving multiple steps and exchanging of multiple instruments, such as needles, stylets, guide wires, catheters, and the like.

The exchanging of multiple instruments complicates the endoscopic procedure, and raises the possibility of contamination each time one of the instruments is changed out. For instance, the exchange of multiple instruments increases the risk of peritonitis caused by leakage of bile juice. Additionally, complications can arise due to leakage during instrument exchange, bleeding, and guide wire displacement.

Accordingly, there is a need for a universal access apparatus that can be used from puncturing to dilation in any EUS procedure, and reduces complications, procedure time, and cost, in addition to allowing for interchange between more than one instrument during a procedure without requiring complete removal of an instrument when that instrument is not in use.

SUMMARY

The disclosed embodiments include an apparatus for insertion into a body through a working channel of an endoscope. The apparatus includes a catheter including a dilator, a guide tube disposed in a lumen of the catheter, and a handle including a puncturing actuator operatively coupled to the proximal end of the guide tube. The dilator may be a cautery device and/or a balloon. The apparatus may also include a stylet needle that includes a cutting distal end for puncturing tissue and extends through a lumen in the guide tube. The handle may also include a stopper that is detachably coupled to the puncturing actuator to fix a position of the puncturing actuator on the handle, and moveable on the handle independently of the puncturing actuator when detached from the puncturing actuator.

The disclosed embodiments also include a method for forming a passageway in a wall of a hollow body organ. The method includes inserting an apparatus including a puncture device and a catheter into a working channel of an endoscope, and positioning a distal end of the endoscope near the wall of the hollow body organ. The puncture device, which includes a guide tube and a stylet needle having a cutting distal end, is advanced across the wall of the organ to form a passageway. The stylet needle is removed from the guide tube, and then a guide wire is inserted through the guide tube such that a distal end of the guide wire extends beyond a distal end of the guide tube. Next, the catheter, which includes a balloon disposed at a distal end portion thereof, is advanced over the guide tube into the organ, and the passageway is enlarged by inflating the balloon.

Many modifications are possible without materially departing from the teachings of the detailed description. Accordingly, such modifications are intended to be included within the scope of the disclosure as defined in the claims.

BRIEF DESCRIPTION OF THE DRAWINGS

These and other aspects and features of the invention will become apparent to those of ordinary skill in the art upon review of the following description in conjunction with the accompanying figures.

FIG. 2A shows an apparatus according to the disclosed embodiments in which the handle is in the start position.

FIG. 2B shows a cross-sectional view of the apparatus along line 2B-2B in FIG. 2A.

FIG. 6 shows a detailed view of the insertion portion according to the disclosed embodiments.

FIG. 7 shows a detailed view of the insertion portion according to the disclosed embodiments.

FIG. 10 shows a detailed view of a proximal end portion of the handle.

FIG. 11 shows a cross-sectional view of a proximal end portion of the handle.

FIGS. 13A-13H show an apparatus according to the disclosed embodiments in various states of use.

FIGS. 14A-14G show a method of performing an EUS procedure using an apparatus according to the disclosed embodiments.

DETAILED DESCRIPTION OF EMBODIMENTS

The disclosed embodiments have been devised to address the above-mentioned problems. In particular, the disclosed embodiments include an apparatus that can be used to access and form passageways in the wall of hollow body structures, such as organs, lesions, cysts, pseudo cysts, and abscesses. The apparatus can be used from puncture to dilation to form a passageway for all EUS drainage procedures. For example, the apparatus can form a passageway from the stomach to intrahepatic bile duct, from the stomach to pancreatic duct, from the stomach to pancreatic cyst, from the duodenum to common bile duct, from the duodenum to gallbladder, and the like. The apparatus can alternate between puncturing and dilation without having to interchange between endotherapeutic tools by completely removing one device for another, thereby reducing the risk of bile leak when tools are changed. Additionally, the disclosed embodiments provide a more stable device that prevents unintentional movement of the guide tube and stylet needle (when present), thereby reducing unintentional trauma or injury to the tissue. Thus, the disclosed embodiments reduce complications, procedure time, and cost.

Various implementations are now described in detail in relation to the drawings. These exemplary implementations of the inventive principles are intended as illustrative only since numerous modifications and variations will be apparent to those skilled in the art.

The disclosed embodiments include an apparatus for insertion into a body through a working channel of an endoscope, and a method for forming a passageway in a wall of a hollow body structure, as described below.

Figure 1:
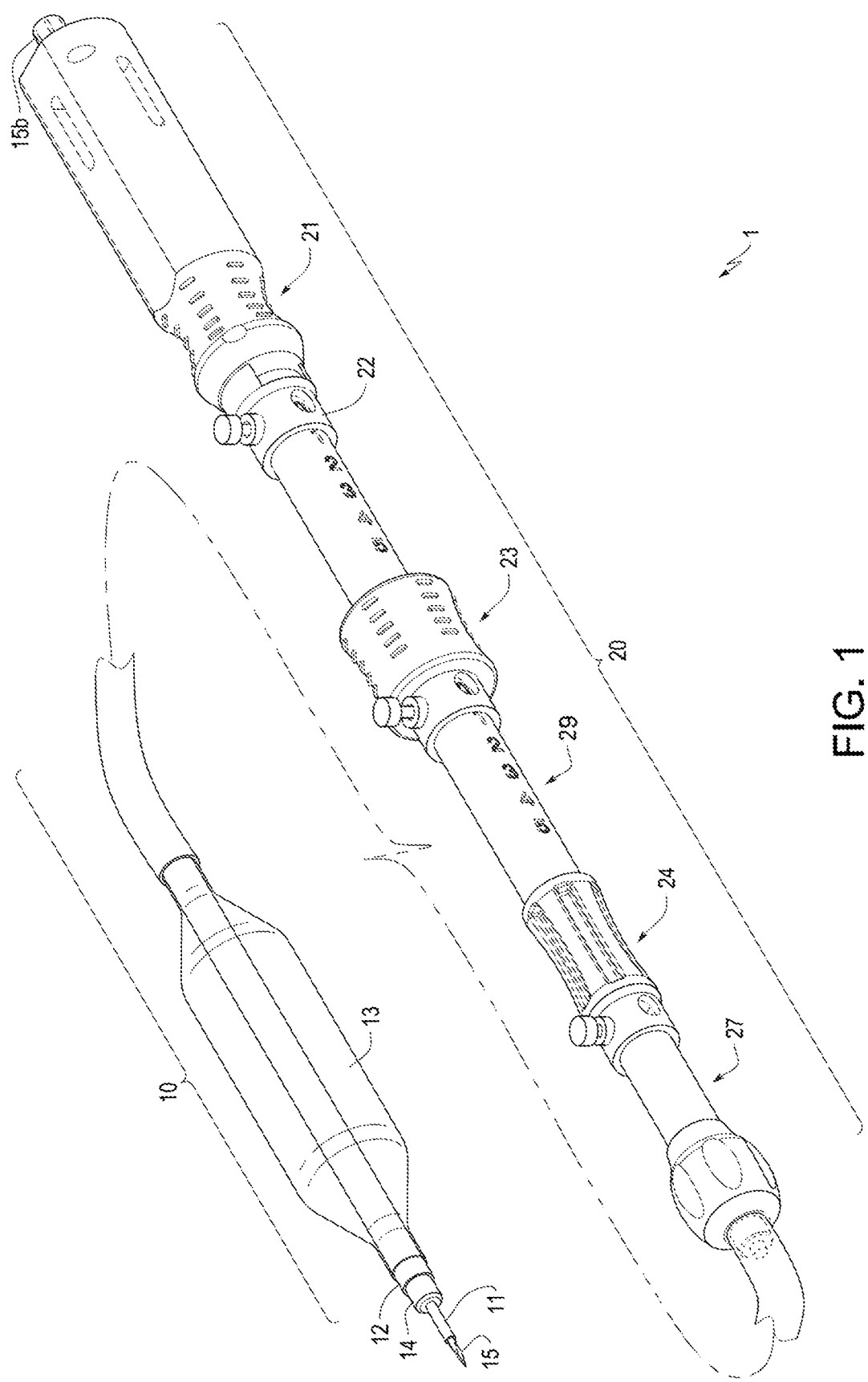
FIG. 1 shows an apparatus according to the disclosed embodiments.

FIG. 1 shows an exemplary apparatus 1 including an insertion portion 10 and a handle 20. The insertion portion 10 is configured to be inserted into a body cavity, and includes a catheter 12 and a guide tube 11 extending through an inner lumen 121 (shown in FIG. 3) of the catheter 12. A cutting stylet needle 15 may be introduced in an inner lumen 111 (shown in FIGS. 8 and 11) of the guide tube 11 for facilitating puncturing of the target site. The catheter 12 includes an inflatable balloon 13 and a cautery device 14 for dilating the punctured target area to a sufficient diameter for placement of a drainage or other device, such as a stent, although other configurations of the catheter 12 may be possible.

The apparatus 1 may be designed for use in conjunction with an endoscope 30 (shown in FIG. 12), such as an ultrasound endoscope, or the apparatus 1 may be used on its own without an endoscope. When used with an endoscope 30, the insertion portion 10 is designed to be introduced through a working channel of the endoscope 30, and a distal end portion 27 of the handle 20 may be coupled with the endoscope 30 via connector 27a. The insertion portion 10 is designed with a sufficient length, strength, flexibility, pushability, and trackability to be operated through an endoscope 30.

The handle 20 is designed to be held by an operator, such as a physician, to support the apparatus 1 while operating one or more of the actuators 21, 23, and 24 and/or the stopper 22, which are moveably coupled to the handle 20. The actuators 21, 23, and 24 are operatively coupled to the catheter 12, guide tube 11, and stylet needle 15 to regulate movement thereof. The handle 20 enables movement of the catheter 12, guide tube 11, and stylet needle 15 to be easily and conveniently controlled by the actuators 21, 23, 24, and the stopper 22, thereby improving efficiency of a previously complicated and lengthy procedure. For example, when the apparatus 1 is connected to an endoscope 30, an operator can easily operate the apparatus 1 with one hand.

As shown in FIGS. 2A-2G, a puncturing actuator 21 is provided on a proximal end of the handle 20 and is operatively coupled to a proximal end 11b of the guide tube 11 and a proximal end portion (near proximal knob 15b) of the needle 15 (see FIG. 2E) so as to regulate movement of the guide tube 11 and needle 15 along a longitudinal axis of the insertion portion 10 with respect to the catheter 12. For example, the puncturing actuator 21 may be actuated by sliding the puncturing actuator 21 in a distal direction along the handle 20 to cause the guide tube 11 and stylet needle 15 to advance to puncture the target structure. The guide tube 11 and stylet needle 15 may be retracted by moving the puncturing actuator 21 in a proximal direction along the handle 20.

When the puncturing actuator 21 is in a proximal position (e.g., a starting position), the guide tube 11 and stylet needle 15 are disposed inside the catheter 12, as shown in FIGS. 13A-13B. It is only after the puncturing actuator 21 has been moved (e.g., slid) in a distal direction along the handle 20 that the guide tube 11 and stylet needle 15 protrude from a distal end of the catheter 12, as shown in FIG. 13C. However, to facilitate understanding of the apparatus 1, FIGS. 1, 2A, 2B, 2F, 2G, and 12, show the guide tube 11 and stylet needle 15 protruding from a distal end of the catheter 12 even though the puncturing actuator 21 is in a proximal position (e.g., a starting position).

Adjacent to the puncturing actuator 21 is a stopper 22. The stopper 22 is moveably disposed on the handle 20 and is designed to be detachably coupled with the puncturing actuator 21 to hold the puncturing actuator 21 in place and prevent unintentional movement thereof. The catheter actuator 23 is provided on a distal side of the puncturing actuator 21 and is operatively coupled to a proximal end 12b of the catheter 12 (see FIGS. 2D and 2G) so as to regulate movement of the catheter 12 along a longitudinal axis of the insertion portion 10 with respect to the guide tube 11 and needle 15. Distal of the catheter actuator 23 is the apparatus actuator 24, which is operatively coupled to the apparatus 1 (including the catheter 12, guide tube 11, and needle 15) to regulate movement of the apparatus 1 (i.e., combined movement of the catheter 12, guide tube 11, and needle 15). Operation and details of the handle 20 are discussed in more detail below.

Figure 2E:
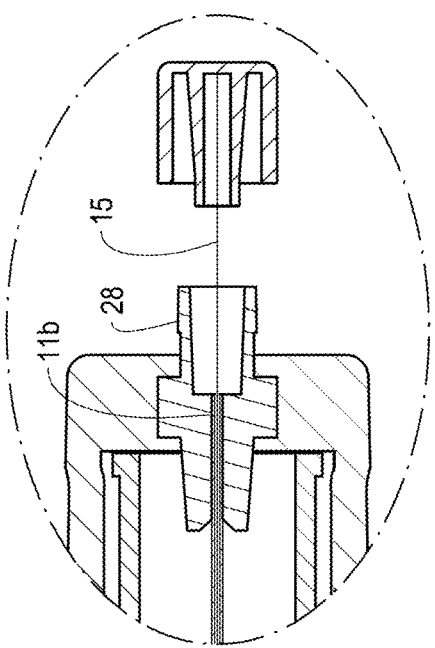
FIG. 2E shows an enlarged view of the circled area labeled 2E in FIG. 2B.
Figure 2D:
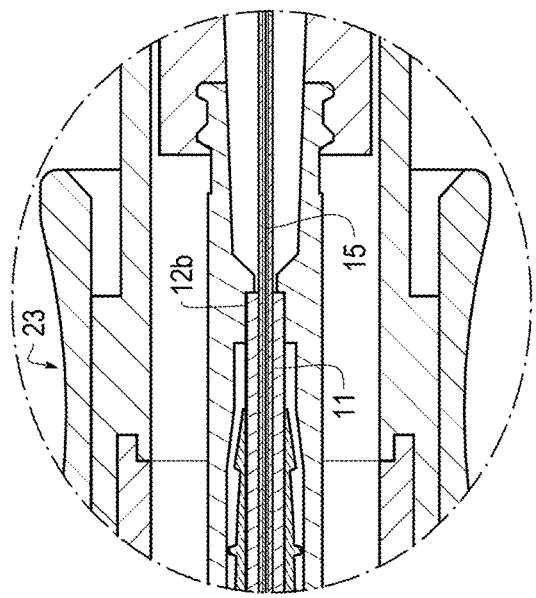
FIG. 2D shows an enlarged view of the circled area labeled 2D in FIG. 2B.
Figure 2C:
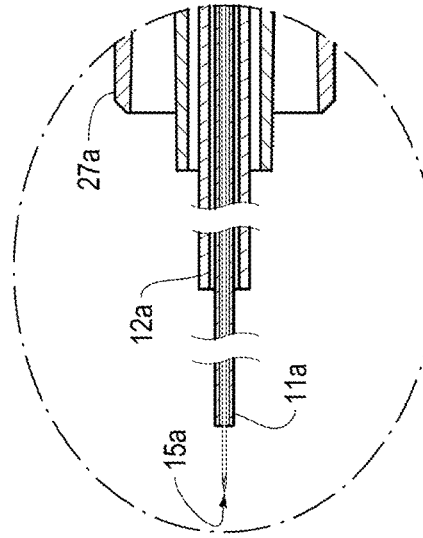
FIG. 2C shows an enlarged view of the circled area labeled 2C in FIG. 2B.
Figure 2F:
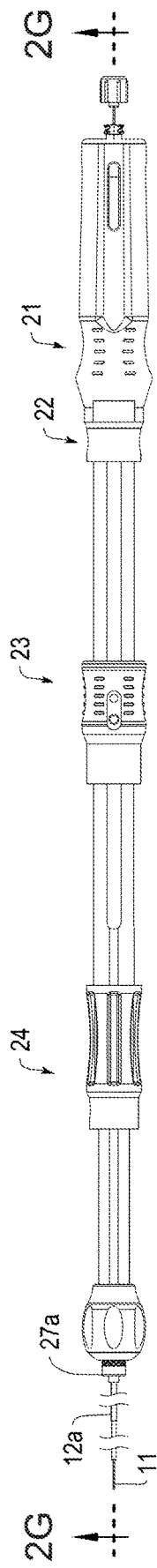
FIG. 2F shows the apparatus rotated about 45 degrees from FIG. 2A.
Figure 2G:
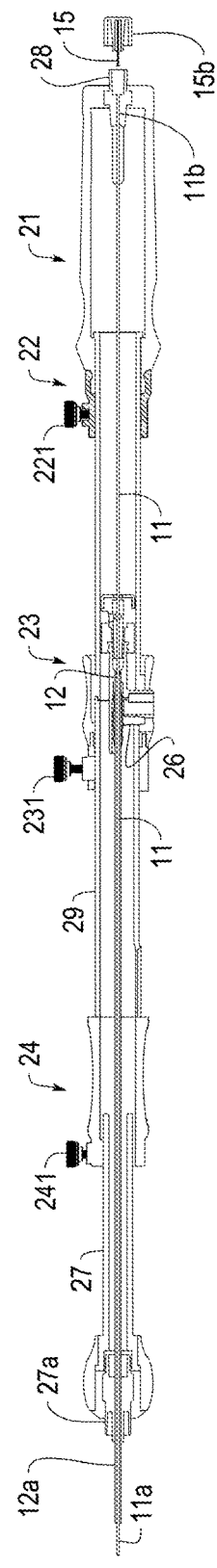
FIG. 2G shows a cross-sectional view of the apparatus along line 2G-2G in FIG. 2F.
Figure 3:
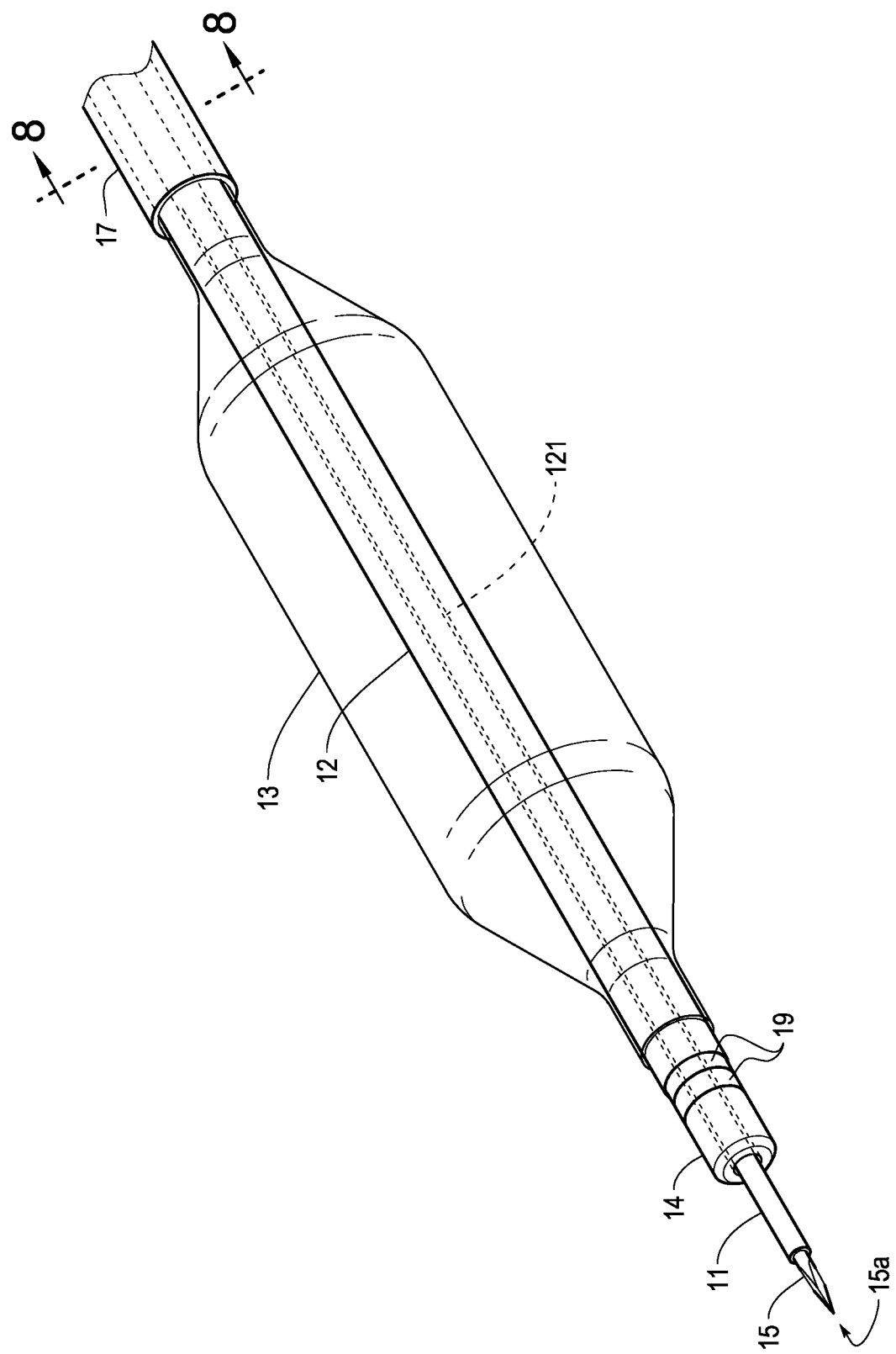
FIG. 3 shows a detailed view of the insertion portion of the apparatus according to the disclosed embodiments.

FIG. 3 shows a detailed view of the insertion portion 10 including the catheter 12, guide tube 11, and stylet needle 15 in a coaxial arrangement. The catheter 12 is a flexible, elongate member extending from a proximal end 12b to a distal end 12a (shown in FIGS. 2B and 2G). The catheter 12 may be constructed from any suitable material, such as polymers, metals, spring coils, silicone, or Teflon tubing. The catheter 12 may include at least one dilator for dilating the initial punctured passageway to a sufficient diameter for placement of a drainage or other device, such as a stent. For example, as shown in FIGS. 1 and 3, the catheter 12 includes a cautery device 14 disposed at its distal end 12a and an inflatable balloon 13 disposed on a proximal side of the cautery device 14.

When the apparatus is a three-in-one apparatus, such as that illustrated in FIGS. 1 and 3, it can be used to perform three functions: puncturing, cauterizing, and expanding (e.g., dilation) by balloon for forming a passageway between hollow body structures for EUS drainage procedures. The three-in-one apparatus can reduce procedure time and complications by allowing interchanging between the devices without requiring complete removal of one device for another. For instance, the apparatus can alternate between puncturing, cauterizing, and balloon expansion functions without having to change between endotherapeutic devices by completely removing one device in order to introduce another, thereby reducing the risk of bile leak when tools are changed.

Other configurations of the catheter 12 may be possible. For example, the catheter 12 may include only the cautery device 14. Sufficient dilation of the punctured area may be obtained by the cautery device 14 by itself in some circumstances, such as when the hollow body structure is small. Alternatively, it may be desirable to dilate the punctured area by the cautery device 14 and the balloon 13 under some circumstances, such as when the target structure is large.

The cautery device 14 increases the penetration force of the catheter 12. If the penetration force is weak, the target structure (e.g., a cyst) may be pushed by the catheter 12 without sufficiently puncturing the structure when approaching the cyst through the stomach wall. This can result in a gap between the stomach wall and the cyst. If there is a gap, the liquid in the cyst or other target structure may leak into the body cavity which may cause complications during the procedure. This is especially important when targeting the gallbladder because the gallbladder is not fixed. The disclosed apparatus 1 including a cautery device 14 provides a high penetration force without pushing the target structure, and thereby prevents complications due to leakage from the target structure into the body cavity. The high penetration force is also important because the stomach wall is thick and sometimes the catheter penetrates the target structure diagonally, making the penetration distance through the thick stomach wall even longer. Additionally, heat from the cautery device 14 can also prevent bleeding, thereby further reducing complications during the procedure.

The catheter 12 includes at least one inner lumen. For example, the catheter 12 includes a main lumen 121 extending from the distal end 12a to the proximal end 12b. The main lumen 121 is designed to slidably receive the guide tube 11 such that the catheter 12 and the guide tube 11 are longitudinally moveable together or with respect to one another. The catheter 12 may be a multi-lumen extrusion including more than one lumen. For example, as discussed below, the catheter 12 may further include a cautery wire lumen 122 through which a cautery wire 141 extends, and/or an inflation lumen 171 designed to transmit fluid for inflating or deflating the balloon 13 (see FIGS. 8 and 9).

Figure 4:
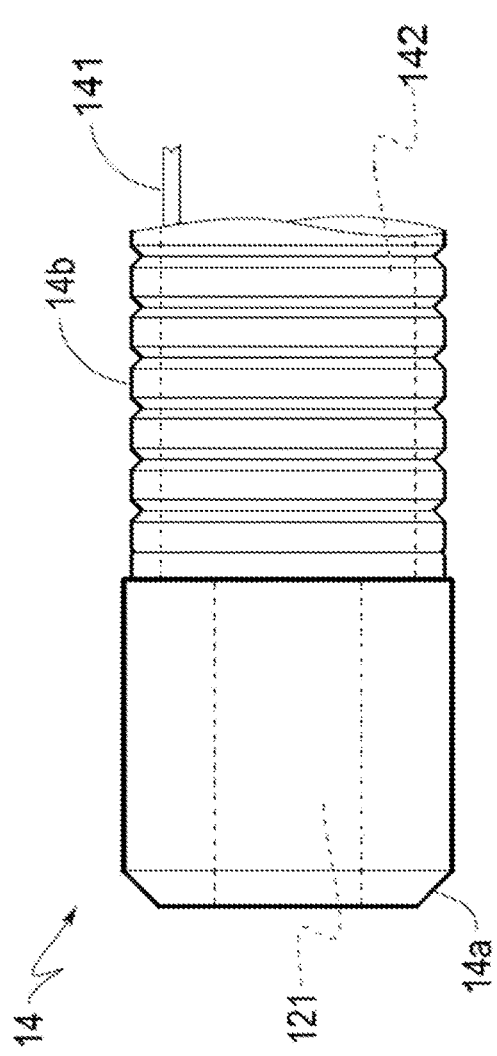
FIG. 4 shows a detailed view of a cautery device according to the disclosed embodiments.

FIG. 4 shows a detailed view of the cautery device 14. The cautery device 14 may be formed as a conductive ring coupled to a distal end of the catheter 12 (see FIG. 5), or the cautery device 14 may have any other suitable shape. For example, the cautery device 14 have a tapered distal end 14a so that an outer diameter of the cautery device 14 increases from a distal end toward a proximal end 14b in the axial direction. The distal end 14a may be tapered at an angle of, for example, 45° or any other suitable angle. In such embodiments, the outer shape of the cautery device 14 may be described as frustoconical. Alternatively, the cautery device 14 may have a cylindrical shape in which the distal end is not tapered, or the cautery device may have any other suitable shape so long as the guide tube 11 can pass therethrough. The cautery device 14 may be sized at about 6 Fr to about 10 Fr, or may be suitably sized to be larger or smaller for various applications. A smaller diameter cautery dilator sized at about 6 Fr to about 7 Fr may be used in some embodiments to avoid a bleeding risk associated with larger diameter cautery devices.

Figure 5:
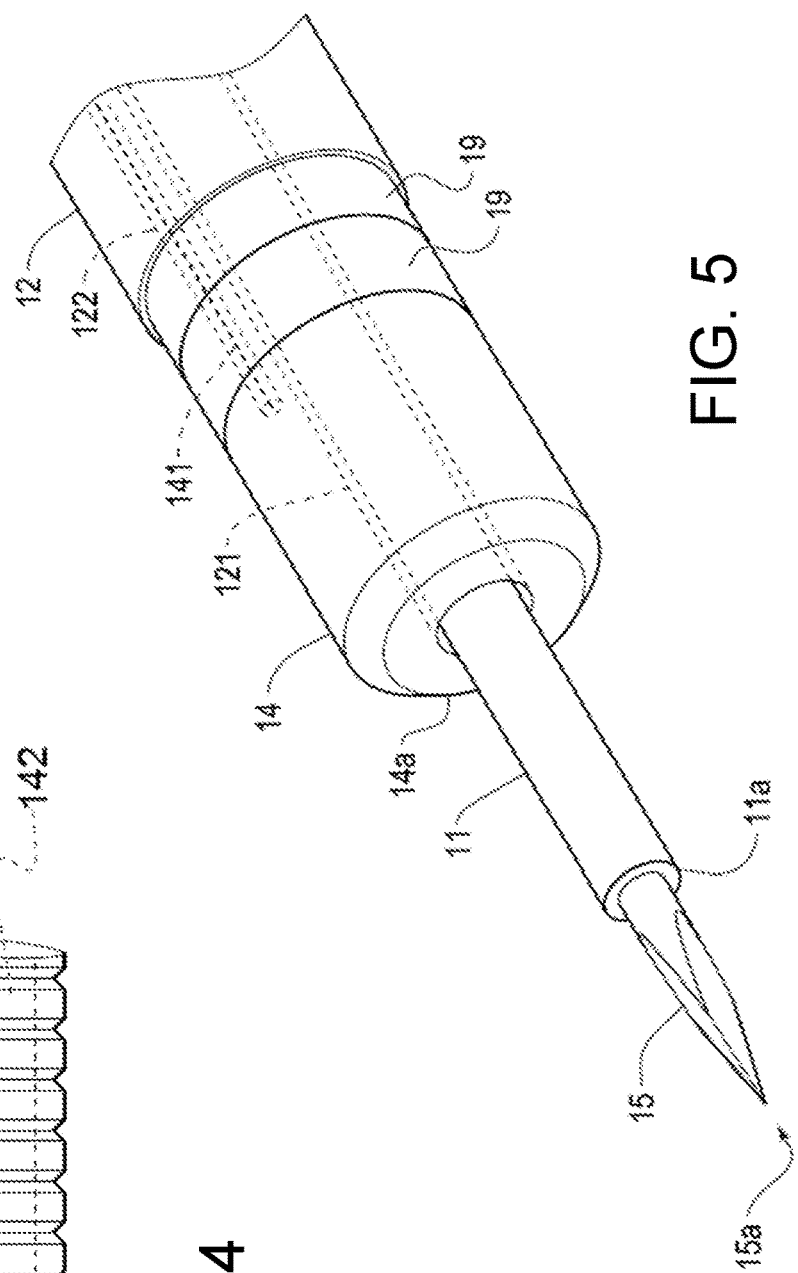
FIG. 5 shows a detailed view of the distal end of the insertion portion according to the disclosed embodiments.

As shown in FIG. 5, the cautery device 14 may be designed as a conductive ring that circumferentially forms or is coupled to the distal end 12a of the catheter 12. For example, a proximal end portion 14b of the cautery device 14 may include a lumen 142 sized to receive a distal end of the catheter 12. The catheter 12 may be bonded to the proximal portion 14b, for example by polyethylene terephthalate (PET) bonding, to create a mechanical lock. It should be appreciated that any other suitable connection means may be used to securely attach the cautery device 14 to the catheter 12. For example, such connection means may include one or more of an adhesive, welding, bolts, screws, friction-fit, and the like.

Figure 9:
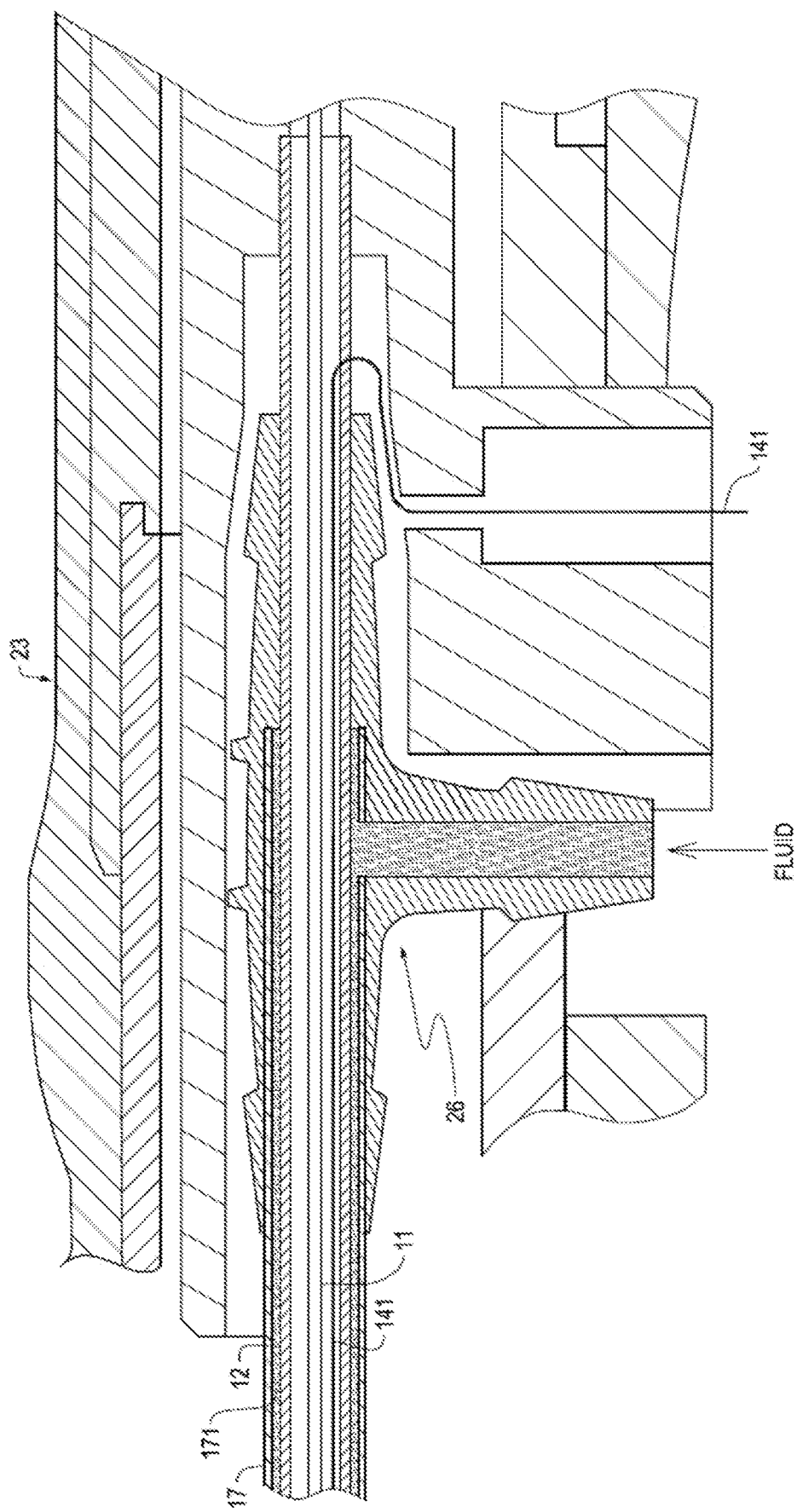
FIG. 9 shows a cross-sectional view of a portion of the handle adjacent to the catheter actuator.

The cautery device 14 is designed to be electrically coupled to an electroconductive element, such as a cautery wire 141 shown in FIG. 4. A distal end of the wire 141 is designed to be electrically coupled to the cautery device 14. For example, a distal end of the wire 141 may be welded to an inner diameter of lumen 142 of the cautery device 14. As shown in FIG. 5, the wire 141 is designed to extend through a wire lumen 122 in the body of the catheter 12 so as to be connected to an electrosurgical power supply (not shown) to transmit energy, such as electric current or radio frequency energy, through the wire 141 to the cautery device 14. For example, as shown in FIG. 9, a proximal end of the cautery wire 141 may extend through the handle 20 at a position near the catheter actuator 23 to connect to an electrosurgical power supply. To use the cautery device 14, the catheter 12 may be advanced until the cautery device 14 contacts the penetrated area of the target site, and the cautery element 14 may be actuated by, for example, directing electrosurgical current from a power supply through the wire 141 and into the cautery device 14 to dilate the target site.

Insulating or non-conductive material may be used to limit exposure of the conductive surface of the cautery element 14. For example, as shown in FIGS. 3 and 5, the catheter 12 may include one or more insulating rings 19 to limit exposure of the conductive surface of the cautery ring 14 to the body of the catheter 12, and/or the body of the catheter 12 may be made mostly or entirely of non-conductive material to prevent conduction from the cautery device 14 through the body of the catheter 12. Additionally or alternatively, the lumen 122 in the catheter 12 through which the cautery wire 141 extends may be coated with insulating or non-conductive material to similarly prevent conduction from the wire 141 through the body of the catheter 12, and/or wire 141 may be electroinsulated. Similarly, insulating material may be used to electrically insulate the guide tube 11 from the cautery device 14.

The catheter 12 may additionally or alternatively include an inflatable balloon 13 for dilating the punctured portion of the target site to a diameter sufficient for placement of a drainage or other device, such as a stent. FIGS. 3, 6, and 7 show exemplary embodiments of the balloon 13. The balloon 13 may be inflated without anchors (FIGS. 3 and 6) or with anchors (FIG. 7), or may have any other suitable inflation configuration. Anchored balloons may be used, for example, to prevent the balloon from slipping off of the organ.

As shown in FIGS. 3, 6, and 7, a proximal end of the balloon 13 is attached to a distal end of an outer jacket 17 formed around the catheter 12, and a distal end of the balloon 13 is attached to the catheter 12 adjacent to insulating rings 19. The balloon may be attached to the outer jacket 17 and catheter 12 by any suitable means, such as bonding. At a proximal end, the outer jacket 17 and the catheter 12 are coupled to a T-connector 26 (shown in FIG. 9) disposed in the handle 20 adjacent to the catheter actuator 23. The T-connector 26 forms a port for a fluid supply device (not shown) such that fluid can be introduced into the T-connector and flow through the inflation lumen 171 (shown in FIGS. 8 and 9) between the outer jacket 17 and the catheter 12 to inflate the balloon 13. Thus, the outer jacket 17 forms an inflation lumen 171 through which fluid is transmitted to inflate or deflate the balloon 13. Other configurations of the inflation lumen may be possible. For example, an inflation lumen (not shown) may be formed in the body of the catheter 12 so as to be in fluid communication with the balloon 13 formed on the outer surface of the catheter 12.

The balloon 13 may be formed of a material having elasticity, and is configured so as to inflate while increasing its diameter gradually as fluid, such as a liquid or gas, stagnates within the balloon. As the materials of the balloon 14, for example, materials such as crude rubber, synthetic rubber, polyurethane, polyamide-based elastomer, and silicon may be used. The balloon material may be substantially transparent, translucent, or a combination thereof, and allow for clear visualization of markers 18 (FIG. 6), which may be contained inside the balloon. Balloon length, measured from the distal most end of the balloon 13 to the proximal most portion of the balloon 13 (attached to jacket 17), may be any suitable length, such as a length in the range of about 30 mm to about 100 mm, about 60 mm to about 80 mm, or about 65 mm to about 75 mm. An inflation diameter of the balloon 13 may be any suitable diameter, such as one in a range of from about 5 to about 20 mm, about 8 to about 15 mm, or about 10 to about 12 mm.

In FIG. 6, an outer surface of the catheter 12 includes marker bands 18, which indicate the length of the balloon under X-ray. Functionally, the purpose of the marker bands 18 is to indicate to the user that the balloon 13 has been advanced sufficiently beyond the face of the endoscope and that it is safe to begin inflation as well as to provide the ability to center the balloon 13 about the geometric center of the penetrated portion to prevent balloon migration. The marker bands 18 may be discernible through the folded or deflated balloon material prior to inflation and through the side wall of the balloon 13 during and after inflation.

As discussed below, to use the balloon 13, the catheter 12 may be advanced until the balloon 13 in a deflated state contacts the penetrated portion of the target site. Then, fluid may be directed from a fluid supply device (not shown) into the port formed by the T-connector 26 in the handle 20 and through the inflation lumen 171 to inflate the balloon 13 and dilate the target penetrated portion to a sufficient diameter for placement of a stent or other device.

As shown in FIGS. 2B, 2C, 2E, 2G, 3, and 8 the guide tube 11 is an elongate tube having a distal end 11a and a proximal end 11b, and an inner lumen 111 extending therethrough. The guide tube 11 is designed to extend through the inner lumen 121 of the catheter 12 so as to be longitudinally moveable independently of and together with the catheter 12. For instance, the guide tube 11 may be advanced with respect to the catheter 12 such that the distal end 11a of the guide tube 11 protrudes from a distal end 12a of the catheter 12. As shown in FIG. 5, the guide tube 11 may be designed to have a blunt or non-pointed distal end 11a to avoid unintentionally puncturing or injuring tissue and/or organs. However, any suitable shape can be used as long as the guide tube 11 can pass through the inner lumen 121 of the catheter 12. For example, the distal end 11a may be rounded or tapered to eliminate sharp edges to reduce the possibility of unintentional injury or trauma to the tissue or organs by the guide tube 11.

The guide tube 11 may be made of a metal or polymer material, or any other suitable material. For example, the guide tube 11 may be made of stainless steel, polyimide, and/or polytetrafluoroethylene (PTFE). At least a distal end portion of the guide tube 11 is designed to be flexible. For example, at least the projecting portion of the guide tube 11 from the distal end 12a of the catheter 12 may be flexible. The flexible distal end portion may facilitate movement of the guide tube 11 through the catheter 12 and along the organ surface. Additionally, a flexible distal end potion of the guide tube 11 may facilitate advancement of the guide tube through tortuous anatomy.

For example, a stainless steel guide tube 11 or at least a distal end portion thereof may be processed by laser cutting so as to impart flexibility. The laser cut distal portion of the guide tube 11 may have a length of at least 60 mm from the distal tip. For example, the laser cut distal portion of the guide tube may have a length of about 60 to 250 mm, or about 75 to about 150 mm, or about 85 to about 110 mm starting from the distal tip.

Laser processing of at least a distal end portion of the guide tube 11 may be advantageous not only because it increases flexibility of the guide tube 11, but it improves visibility under ultrasound. A laser processed stainless steel guide tube 11 may have a cylindrical shape with gaps similar to a compressed spring. This structure improves flexibility of the guide tube 11 for accessing tortuous anatomy while also enabling excellent pushability and trackability through the apparatus 1. Additionally, when the apparatus 1 is used in connection with an ultrasound endoscope 30, visibility is improved by the laser processed surface. Ultrasound endoscopes capture the reflection of sound so creating irregularities or dimple processing on the surface of a device can be used to improve visibility of the device. Laser processing has the advantage of improving both flexibility and visibility under ultrasound endoscopy.

The distal end portion 11a of the guide tube 11 may also be visible under X-ray. For example, an outer surface of the distal end portion 11a of the guide tube 11 may include marker bands, like the marker bands 18 shown on the catheter 12 in FIG. 6. The marker bands permit a user to visualize the position of the guide tube 11 under X-ray, and/or determine a length of the guide tube 11 protruding from a distal end 12a of the catheter 11.

The stainless steel guide tube 11 or a portion thereof may be covered with an insulating material, such as polyethylene terephthalate (PET) heat shrink extrusion. When the guide tube 11 includes marker bands for visibility under X-ray, one or more marker band may be provided on an outer surface of the PET heat shrink extrusion. The PET heat shrink extrusion electrically insulates the guide tube 11 from the cautery device 14. For example, if electricity flows through the guide tube 11 (e.g., from the cautery device 14), the electricity may flow through the tissue in contact with the guide tube 11, and the power of the cautery device 14 may be reduced because the current density would be reduced. The PET heat shrink extrusion prevents electricity from flowing through the guide tube 11. The PET heat shrink tube also prevents fluid from leaking out of the laser cut portion of the stainless steel guide tube 11. For example, the PET heat shrink extrusion can prevent leakage of a contrast agent injected into the body or fluid extracted from the body from leaking out of the gaps or openings in the laser processed portion of the guide tube 11. In such embodiments, the PET heat shrink extrusion may be longer than the laser processed area (e.g., distal end portion) of the guide tube 11 to avoid such leakage. A laser cut stainless steel guide tube 11 with a PET heat shrink extrusion has excellent insertability, puncturability, and material strength for use in EUS procedures.

Other configurations of the guide tube 11 may also be possible. For example, the guide tube 11 may be a braid reinforced polyimide tube including an inner polyimide/polytetrafluoroethylene (PTFE) liner, an outer polyimide layer, and a layer of braided wire in between, or the guide tube 11 may have any other suitable configuration.

The inner lumen 111 of the guide tube 11 may be designed to receive a stylet needle 15 and/or a guide wire 16. For instance, as shown in FIGS. 2A-2G, the stylet needle 15 may extend through the inner lumen 111 of the guide tube so as to protrude from a distal end 11a thereof. The stylet needle 15 may be a flexible, elongate member extending from a proximal knob 15b to a cutting distal end 15a designed to facilitate puncturing of the target tissue. For example, the stylet needle 15 may be a solid, slender probe-like member with a puncturing distal end 15a. The cutting stylet 15 may function as a puncture needle and is operated in combination with the guide tube 11 to perform the puncturing step. Therefore, the cutting distal end 15a may be, for example, a sharp or pointed distal end to facilitate puncturing the tissue. Due to its cutting distal end 15a, the stylet needle 15 may be removed from the apparatus 1 after the puncturing step and before the dilation step to avoid complications arising from injury or trauma to the organ or tissue due unintentional contact with the cutting distal end 15a of the stylet 15, especially during dilation.

As mentioned above, the stylet needle 15 may be used in combination with the guide tube 11 to puncture the target tissue to create an initial passageway in a wall of a hollow body structure. The guide tube 11 and cutting stylet needle 15 may be collectively referred to as "a puncture device." The stylet 15 and guide tube 11 are designed to be advanced or retracted together along the longitudinal axis of the apparatus with respect to the catheter 12. During puncturing mode, the stylet needle 15 is inserted into the lumen 111 of the guide tube 11. The combination of the stylet needle 15 and the guide tube 11 provides a stiffness that facilitates puncturing of the target tissue. After puncturing the tissue, the stylet needle 15 is removed from the lumen 111 of the guide tube 11 by retracting the proximal knob 15b. After removal of the stylet needle 15, the flexibility of the guide tube 11 is increased, thereby enabling an operator to advance the guide tube 11 along the inner surface of an organ with a reduced likelihood of causing trauma or injury to the organ.

The stylet needle 15 may be made of any suitable material, including metal and polymer materials. For example, the stylet needle 15 may be made of materials that are elastically deformable so that the needle 15 is bendable. The stylet needle 15 may be made of shape memory material, such as nitinol, so that the stylet needle 15 returns to its original shape after being bent. Although the figures show the stylet needle 15 having a sharp or pointed (e.g., cutting) distal end, the stylet needle 15 and its distal end 15a could have any suitable configuration.

As shown in FIGS. 13F-13H and 14D-14G, the inner lumen 111 of the guide tube 11 may be designed to receive a guide wire 16 after puncturing the target tissue area to create an initial passageway through the wall of the luminal body structure and removing the stylet needle 15. The guide wire 16 may provide a degree of rigidity or firmness to the flexible portion of the guide tube 11 to facilitate advancement of the catheter 12 over the guide tube 10 to initial the dilation step. For example, the guide wire 16 may extend through the guide tube 11 into the luminal body structure such that when the catheter 12 is advanced over the guide tube 11, the guide tube 11 is prevented from slipping off the organ. The guide wire 16 may also be used after the passageway has been sufficiently dilated. For example, a stent or other device may be advanced over the guide wire 16 to complete the drainage procedure.

Figure 13D:
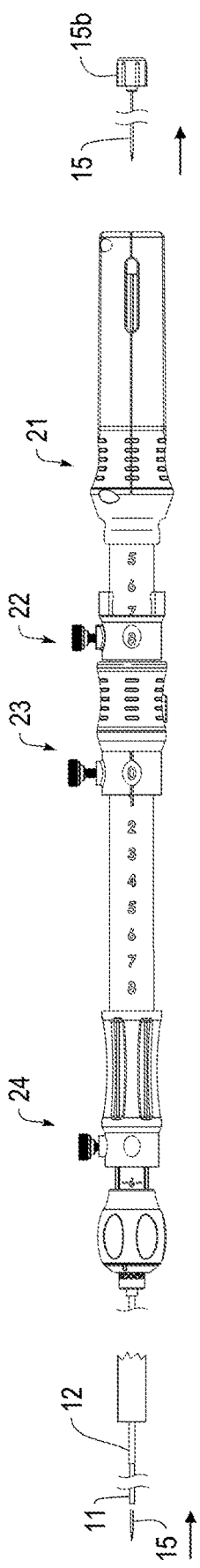
Figure 13E:
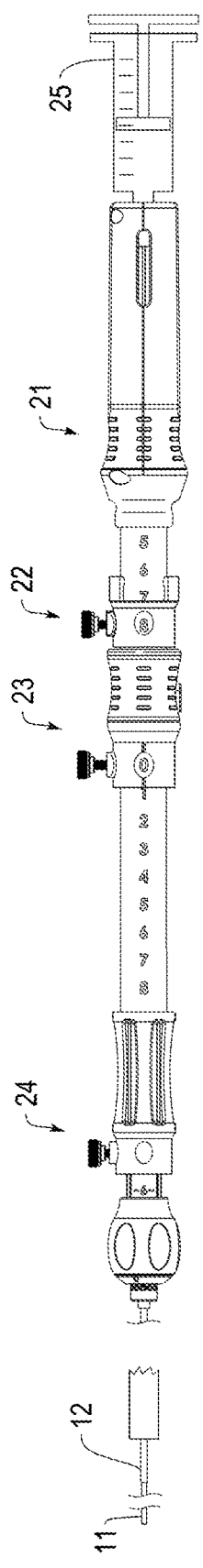
Figure 13F:
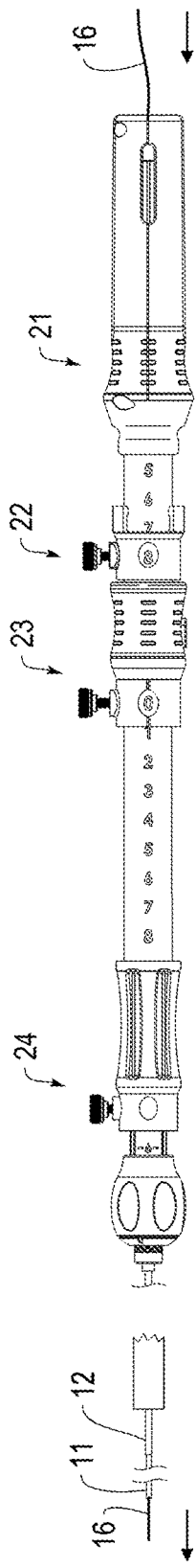
Figure 13G:
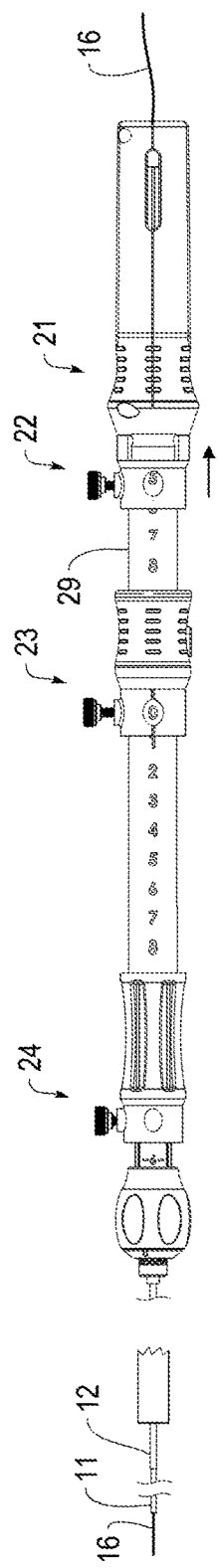
Figure 13H:
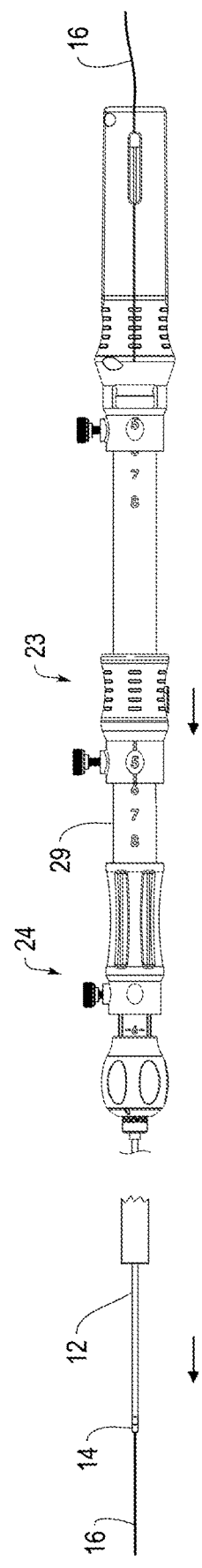

Additionally, the inner lumen 111 of the guide tube 11 may be designed for use in aspiration and/or injection procedures, as shown in FIG. 13E. For example, a proximal end of the handle 20 may include a dedicated port, such as connector 28, for receiving a stylet needle 15, guide wire 16, or an aspirator/injector 25. The flexible end portion 11a of the guide tube 11 enable aspiration and/or injection to be performed without causing injury or trauma to the organs.

Figure 8:
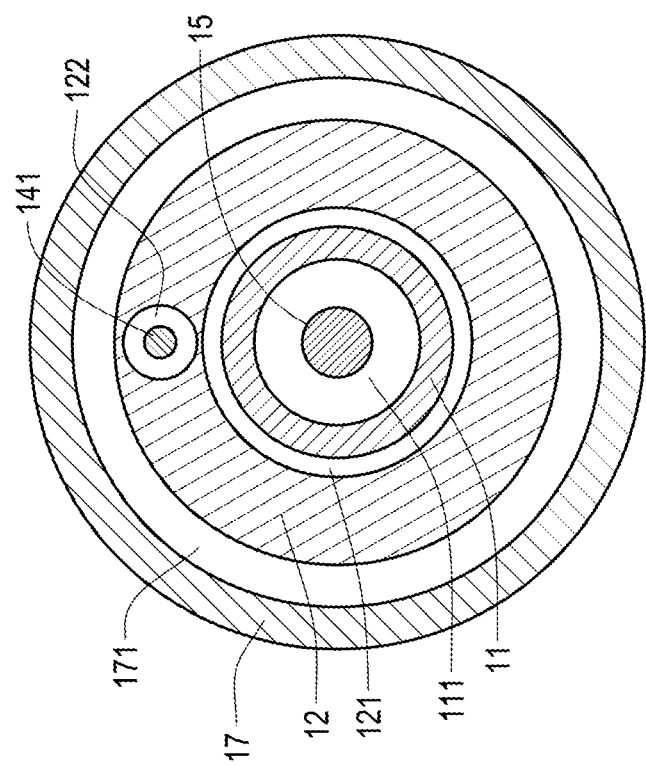
FIG. 8 shows a cross-sectional view of the insertion portion along line 8-8 in FIG. 3.

FIG. 8 shows a cross-section view of the insertion portion 10 along line 8-8 in FIG. 3. As shown in FIG. 8, the stylet needle 15 is disposed in the lumen 111 of the guide tube, which is moveably disposed in the main lumen 121 of the catheter 12. The catheter 12 may also include a lumen 122 for the cautery wire 141. Additionally, at least part of the catheter 12 (e.g., proximal of the balloon 13) may be surrounded by an outer jacket 17 such that an inflation lumen 171 is formed between the outer jacket 17 and the outer surface of the catheter 12. Alternatively, an inflation lumen may be formed in the multi-lumen extrusion of the catheter 12 so as to be in fluid communication with the balloon 13.

As mentioned above, the apparatus includes a handle 20 operatively coupled to a proximal end of the insertion portion 10. The handle 20 is configured to be held by an operator during an endoscopic procedure, and to be operated to independently or collectively advance or retract the guide tube 11, needle 15, and the catheter 12. As shown in 2A-2G, the handle 20 includes a distal handle body 27 and a proximal handle body 29, each of which may have a substantially cylindrical body. The distal handle body 27 and the proximal handle body 29 may be slidably coupled with one another via the apparatus actuator 24 (see FIGS. 2A, 2B, 2F, and 2G). The distal handle body 27 includes connector 27a for connecting the handle to an endoscope 30 (see FIG. 12). The proximal handle body 29 includes a puncturing actuator 21, a stopper, and a catheter actuator 23, which are independently slidably on the proximal handle body 29. A distal end of the proximal handle body 29 forms the apparatus actuator 24, which can be actuated to slide the proximal handle body 29 distally or proximally with respect to the distal handle body 27 and thereby advance or retract the apparatus (i.e., advance or retract the guide tube 11, catheter 12, and needle 15 together). As shown in FIGS. 2A, 2B, 2F, and 2G, the distal handle body 27 and the proximal handle body 29 may include scales indicating a moving distance of each of the actuators 21, 23, and 24. Thus, the scales may also indicate a moving distance of the guide tube 11, needle 15, catheter 12, and apparatus 1. For instance, the proximal handle body 29 may include two scales, one for the puncturing actuator 21 and one for the catheter actuator 23. The distal handle body 27 may include a scale for the apparatus actuator 24.

As shown in FIGS. 2B, 2E, and 2G, the puncturing actuator 21 is slidably coupled to a proximal end of the proximal handle body 29 such that the puncturing actuator 21 can slidably advance or retract along the proximal handle body 29. The puncturing actuator 21 is operatively coupled to the proximal end 11b of the guide tube 11 and the needle 15 (when present). For example, the puncturing actuator 21 may be operatively coupled to the proximal end 11b of the guide tube 11 and a proximal portion of the stylet 15 via a connector 28. The puncturing actuator 21 is configured to be operated to advance or retract the guide tube 11 together with the needle 15 (when present) such that the guide tube 11 and needle 15 move with respect to the catheter 12. When the puncturing actuator 21 is in a proximal position (e.g., a starting position), the guide tube 11 and stylet needle 15 are disposed inside the catheter 12, as shown in FIGS. 13A-13B. However, to facilitate understanding of the apparatus 1, FIGS. 1, 2A, 2B, 2F, 2G, and 12, show the guide tube 11 and stylet needle 15 protruding from a distal end of the catheter 12 even though the puncturing actuator 21 is in a proximal position (e.g., a starting position).

The proximal end 11b of the guide tube 11 may be fixed to the connector 28 formed on a proximal end of the puncturing actuator 21 (see FIG. 2E) by, for example, bonding. The needle 15 may be introduced into the apparatus through the connector 28 on the proximal end of the handle 20 so as to extend through the connector 28 and the guide tube 11 and protrude from a distal end 11a of the guide tube 11 (see FIG. 2C). The needle 15 can be coupled to the guide tube 11 via connector 28, which may be a luer lock connector or any other suitable connector, such that the guide tube 11 and the needle 15 advance or retract together with respect to the catheter 12 in response to actuation of the puncturing actuator 21. For example, as shown in FIGS. 2A-2D, the puncturing actuator 21 may be actuated by longitudinally sliding the puncturing actuator 21 with respect to the handle body 20. When the puncturing actuator 21 is slidably advanced in a direction toward a distal end, the guide tube 11 and needle 15 are likewise advanced in the distal direction. Similarly, when the puncturing actuator 21 is slidably retracted in a proximal direction with, the guide tube 11 and needle 15 are likewise retracted in the proximal direction. Although the puncturing actuator 21 is shown as being a sliding actuator, any other suitable actuating means may be employed so long as it can advance and retract the guide tube 11 and needle 15.

Movement of the puncturing actuator 21 may be regulated by the stopper 22. As shown in FIGS. 10 and 11, the stopper 22 is slidably disposed on the handle 20 and can move independently of the puncturing actuator 21 in a distal or proximal direction. The stopper 22 may be detachably coupled to the proximal actuator 21 to fix a position of the proximal actuator 21 with respect to the handle 20 and prevent unintentional movement of the proximal actuator 21 and guide tube 11, for example, by unintentional bumping of the proximal end of the handle 20.

As shown in FIG. 11, the stopper 22 may be detachably coupled to the puncturing actuator 21 via a snap-fit connection in which a proximal portion 222 of the stopper 22 may be designed to snap onto a distal portion 211 of the puncturing actuator 21. The proximal portion 222 and distal portion 211 may be arms designed to be detachably coupled to one another. The snap-fit arms 222 and 211 permit the stopper 22 and the puncturing actuator 21 to be easily attached and detached from one another. The stopper 22 is designed to hold the puncturing actuator 21 in place on the handle while allowing the puncturing actuator 21 to be easily detached from the stopper 22 by retracting the puncturing actuator 21 in a proximal direction. The separable stopper 22 and puncturing actuator 21 avoid possible complications or injuries caused by accidentally bumping the puncturing actuator 21 by preventing the puncturing actuator 21 from advancing when detachably coupled to the stopper 22. Additionally, by using a separable stopper 22, the puncturing length of the guide tube 11 and stylet needle 15 can be accurately controlled. For example, the puncturing length (e.g., distance the guide tube 11 and stylet needle 15 should advance to sufficiently puncture the target structure) can be determined before the guide tube 11 and needle 15 are pushed into the target structure. The stopper 22 can be appropriately positioned according to the determined puncturing length. As such, even if the puncturing actuator 21 is pushed vigorously, protrusion of the guide tube 11 and needle 15 further than the puncturing length can be prevented by the stopper 21.

The stopper 22 may be designed to lock the puncturing actuator 21 into place by frictional contact between fastener 221 and the outer surface of the proximal handle body 29, as shown in FIG. 11. The fastener 221 may be a screw, tab, rivet, projection, knob, protuberance, or any other suitable structure for stopping distal movement of the puncturing actuator 21 when coupled thereto. Other configurations of the stopper 22 may be possible. For example, instead of a frictional connection between fastener 221 and the proximal handle body 29, the fastener 221 may be designed to engage indents or grooves in the surface of the proximal handle body 29 to hold the puncturing actuator 21 in place.

As shown in FIGS. 2B, 2D, and 2G, the catheter actuator 23 is slidably disposed on the proximal handle body 29 at a position distal of the puncturing actuator 21. The catheter actuator 23 is operatively coupled to a proximal end 12b of the catheter 12 (see FIG. 2D) and is configured to advance or retract the catheter 12 independently of the guide tube 11 (and needle 15 when present). The catheter actuator 23 may be coupled to the proximal end 12b of the catheter 12 via the T-connector 26 (shown in FIGS. 2G and 9). The T-connector 26 may slide along a slot in the proximal handle body 29 when the catheter actuator 23 is advanced or retracted with respect to the handle body 29 so as to advance or retract the catheter 12 with respect to the guide tube 11. Although the catheter actuator 23 is shown as being a sliding actuator, any other suitable actuating means may be employed so long as it can advance and retract the catheter 12.

The catheter actuator 23 may include a stopper 231 to prevent unintentional movement of the catheter actuator 23 along the proximal handle body 29. As shown in FIG. 2A, the catheter actuator stopper 231 is integrally formed with the catheter actuator 23. However, other configurations may be possible. For example, the stopper 231 could be separable and independently moveable from the catheter actuator 23. The stopper 231 may regulate movement of the catheter actuator 23 by frictional contact with the proximal handle body 29. The stopper 231 may be any suitable fastener, such as a screw, tab, rivet, projection, knob, protuberance, or any other suitable structure that is in frictional contact with an outer surface of the proximal handle body 29, or may have any other suitable configuration. Alternatively, stopper 231 may engage indents or a groove on the proximal handle body 29 to regulate movement of the catheter actuator 23.

As shown in FIGS. 2A-2G, the apparatus actuator 24 is disposed on a distal end of the proximal handle body 29 and is slidably coupled to the distal handle body 27. The apparatus actuator 24 is configured to be operated to advance or retract the catheter 12, guide tube 11, and needle 15 (when present) together. That is, the apparatus actuator 24 is designed to be operated to adjust a working length of the apparatus 1. The apparatus actuator 24 may form the distal end of the proximal handle body 29, as shown in FIGS. 2A, 2B, 2F, and 2G. The apparatus actuator 24 is configured to be operated by sliding the actuator 24 distally or proximally along a longitudinal axis of the handle 20. The apparatus actuator 24 is designed to slide along the longitudinal axis with respect to the distal handle portion 27. Because the apparatus actuator 27 is fixed to the proximal handle body 29, movement of the apparatus actuator 24 along the longitudinal axis correlates to movement of the proximal handle body 29 and the proximal and catheter actuators 21, 23 disposed thereon. Therefore, when the apparatus actuator 24 is actuated, the catheter 12, guide tube 11, and needle 15 (when present) collectively move, along with the catheter actuator 23, puncturing actuator 21, and the proximal handle body 29. Although the apparatus actuator 24 is shown as being a sliding actuator, any other suitable actuating means may be employed so long as it can advance and retract the apparatus 1 along a longitudinal axis of the working channel of the endoscope 30.

Similar to the catheter actuator 23, the apparatus actuator 24 includes an integral stopper 241 for fixing a position of the apparatus actuator 24 with respect to the distal handle body 27. The stopper 241 may have any suitable configuration, such as any of those discussed above with respect to the catheter stopper 231 or the puncturing stopper 22. Additionally, although the stopper 241 is shown as being integrally formed with the apparatus actuator 24, it may be separable from the apparatus actuator 24 (e.g., detachably coupled thereto) like stopper 22.

Figure 12:
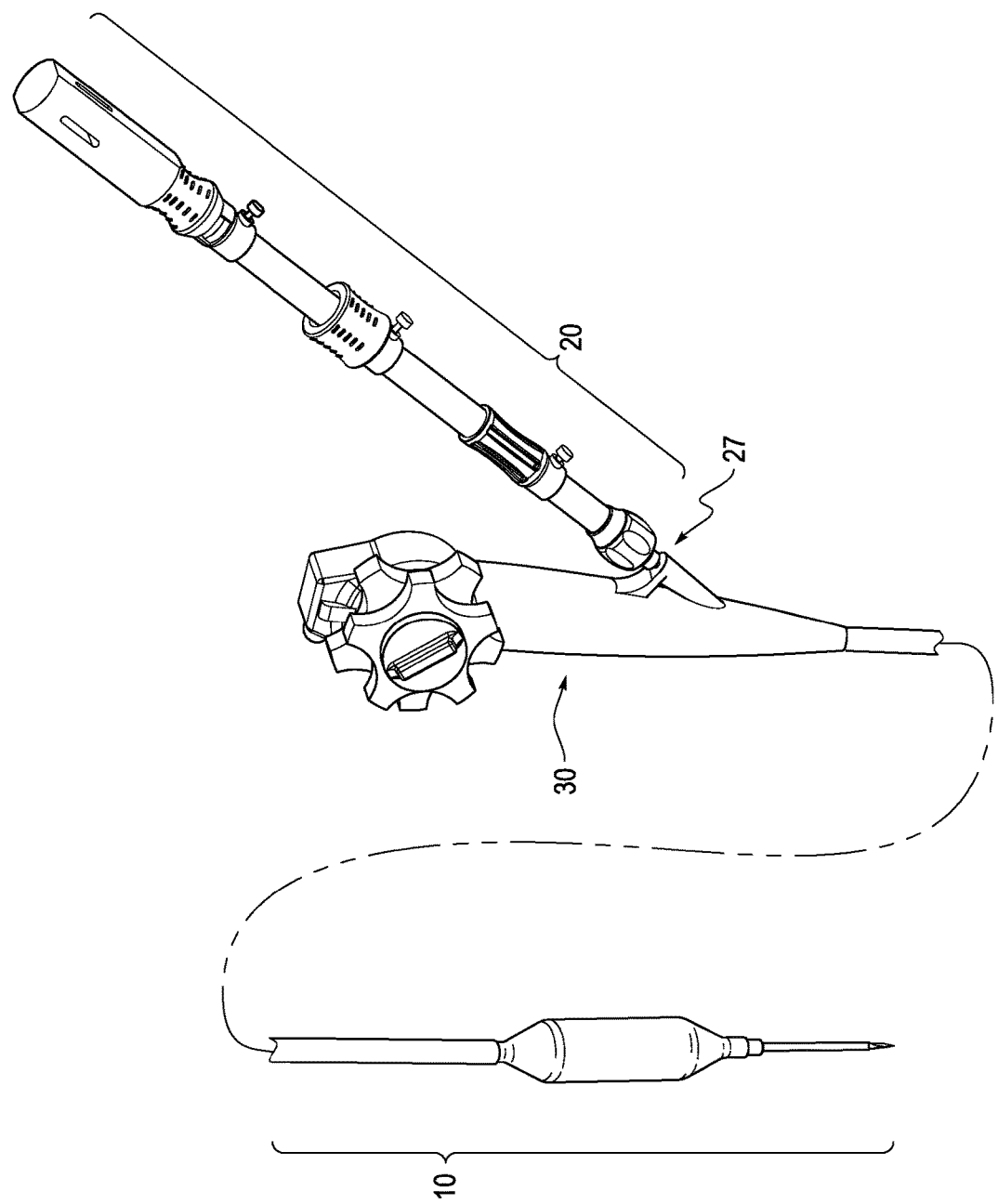
FIG. 12 shows an apparatus according the disclosed embodiments inserted into a working channel of an endoscope.

FIGS. 14A-14G show an exemplary method of using the apparatus to create a passageway between a gastrointestinal tract and a pseudo cyst, although the apparatus 1 may be used to create a passageway in any luminal body structure. FIGS. 13A-13H the apparatus 1, in particular, the handle 20, in various states of use. In the exemplary method, the apparatus 1 is first introduced into the working channel of an endoscope 30, as shown in FIG. 12. The connector 27a on the distal portion 27 of the handle is coupled to the instrument channel port of the endoscope 30. As shown in FIG. 13A, the projecting length of the apparatus 1 from the distal end of the instrument channel may be adjusted by advancing or retracting the apparatus actuator 24 on the handle 20. For instance, the apparatus actuator 24 has been advanced in the distal direction along the handle axis as compared to FIG. 2A.

As shown in FIG. 14A, the apparatus 1 and endoscope 30 are advanced to the target site. The apparatus actuator 24 may be actuated by sliding the actuator 24 in a distal direction to advance the apparatus 1 so that a distal end 12a of the catheter 12 is adjacent to the target site. The guide tube 11 and stylet 15 may be disposed inside the catheter 12 at this time to avoid unintentional injury (e.g., due to the cutting distal end 15a) while advancing the apparatus through the hollow body structure. As shown in FIG. 3A, the puncturing actuator 21 is in a proximal-most position such that the distal end 11a of the guide tube 11 and the distal end 15a of the stylet 15 are disposed inside the catheter 12.

Once the distal end 12a of the catheter 12 is positioned at the target site, the puncturing step may be performed. As shown in FIG. 14B, the guide tube 11 and cutting stylet needle 15 are advanced together to puncture the gastrointestinal tract and the pseudo cyst to form an initial pathway therethrough. As shown in FIG. 13C, the guide tube 11 and cutting stylet needle 15 are advanced during the puncturing step by sliding the puncturing actuator 21 in a distal direction with respect to the longitudinal axis of the handle. The puncturing actuator 21 is not coupled with the stopper 22 during the puncturing step. Before beginning the puncturing step, the stopper 22 may be advanced to a distal-most position (see FIG. 13B) so that it does not interfere with actuation of the puncturing actuator 21 during the puncturing step.

After the target site has been punctured by the guide tube 11 and cutting stylet needle 15, the stylet needle 15 may be removed from the guide tube 11 by pulling the proximal knob 15b in the proximal direction, as shown in FIGS. 13D and 14C. Removal of the cutting stylet needle 15 prevents possible organ damage by the puncturing distal end 15a thereof during the subsequent steps, especially the dilation step. After the cutting stylet needle 15 has been removed, fluid may be aspirated or injected through the guide tube 11 by coupling an aspirator or injector 25 to the connector 28 on the proximal end of the handle 20 (see FIG. 13E). The flexible distal end portion of the guide tube 11 enables the guide tube 11 to be moved across the organ or other body structure during injection and/or aspiration without causing complications, injury, or trauma. Then, a guide wire 16 may be introduced into the guide tube 11 so as to protrude from a distal end 11a of the guide tube 11 (see FIGS. 13F and 14D). The guide wire 16 may be advanced further inside the target structure than the guide tube 11, and may function as an anchor to prevent the guide tube 11 from slipping off the organ or other body structure.

Before beginning the dilation step, the stopper 22 is slid along the handle to be coupled with the puncturing actuator 21 (see FIG. 13G) to hold the puncturing actuator 21 in place and prevent unintentional movement of the puncturing actuator 21 and thus also the guide tube 11, for example, by bumping the end of the handle 20. Although the stopper 22 is shown as being coupled with the puncturing actuator 21 after aspiration and/or injection and after introducing the guide wire through the guide tube 11, the stopper 22 may be coupled with the puncturing actuator 21 any time after the puncturing step and before the dilation step.

In the dilation step, the catheter 12 is first advanced along the guide tube 11 to position the dilator in the punctured target site. A guide tube 11 having a blunt or non-cutting distal end 11a and a flexible distal end portion is advantageous because it reduces unintentional organ damage or trauma that could be caused by a sharp or pointed (e.g., cutting) distal end and/or rigid distal end portion during dilation. The punctured area may be dilated by the cautery device 14 alone, or by both the cautery device 14 and the balloon 13. An apparatus including both the cautery device 14 and the balloon 13 permits an operator to easily perform one or both dilation procedures and to switch between the dilation procedures without having to completely exchange one instrument for another. To cauterize the punctured area, the catheter 12 is advanced by advancing the catheter actuator 23 so as to position the cautery device 14 in a central area of the punctured portion (see FIGS. 13H and 14E). Then, the cautery device 14 is actuated by transmitting energy through the wire 141 from a peripheral power supply in order to expand the diameter of the punctured area.

Balloon dilation may be performed by adjusting the position of the catheter 12 by advanced or retracting the catheter actuator 23 such that the balloon 13 is in a central area of the punctured portion (see FIG. 14F). Then, the balloon 13 is inflated by transmitting fluid from a fluid supply device (not shown) into the port formed by the T-connector 26 through the inflation lumen 171 (see FIG. 9) and into the balloon 13 to expand the outer diameter thereof. The balloon 13 may dilate the punctured portion to a size suitable for placement of a stent or other device. Then, the balloon 13 is deflated, and the apparatus 1 is retrieved from the instrument channel with the guide wire 16 remaining (see FIG. 14G). Alternatively, balloon dilation may be performed before cauterizing the punctured area, or the punctured area may only be dilated by the cautery device 14.

After the apparatus 1 has been removed, a drainage stent or other device may be advanced along the guide wire 16 into the dilated target site for creating a passageway therein to drain fluid or create a conduit between an obstructed target structure. For example, after puncturing and dilating to create a passageway, a drainage device (e.g., drainage stent) may be placed, for example, to drain fluid from the target structure, such as a pseudo cyst in the pancreas, into the bowel, or a stent or other device may be placed to create a conduit between an obstructed target structure, such as an obstructed bile or pancreatic duct, and the bowel.

Although the method illustrated in FIGS. 14A-14G shows puncturing and dilating to create a passageway in the gastric wall and a pseudo cyst, the apparatus and method are not limited to such applications. The apparatus and method may be used to create as passageway (by puncturing and dilation) in any hollow body structure, such as organs, cysts, pseudo cysts, abscesses, lesions, and the like.

The illustrated exemplary embodiments of the apparatus and method as set forth above are intended to be illustrative and not limiting and can be combined. Various changes may be made without departing from the spirit and scope of the invention.

What is claimed is:

1. An apparatus for insertion into a body through a working channel of an endoscope, the apparatus comprising:
    a catheter extending from a proximal end to a distal end, the catheter including a catheter lumen and a dilator;
    a guide tube that extends from a proximal end to a distal end, and is disposed in the catheter lumen, the guide tube including a guide tube lumen configured to removably receive a stylet needle; and
    a handle including:
        a puncturing actuator coupled to the proximal end of the guide tube and configured to be operated to move the guide tube relative to the catheter, and
        a stopper configured to be coupled to the puncturing actuator to hold the puncturing actuator at a position in a predetermined range on the handle or move with the puncturing actuator to a position in the predetermined range on the handle,
    wherein a proximal end portion of the stopper is configured to:
        snap onto a distal end of the puncturing actuator to couple the stopper to the puncturing actuator when the stopper is moved in a proximal direction on the handle, and
        decouple from the distal end of the puncturing actuator when the stopper is moved in a distal direction on the handle.

2. The apparatus according to claim 1, wherein the handle further comprises a catheter actuator coupled to the proximal end of the catheter, and configured to be operated to move the catheter relative to the guide tube.

3. The apparatus according to claim 1, wherein the stopper is configured to be detachably coupled to the puncturing actuator via a snap-fit connection.

4. The apparatus according to claim 1, wherein the puncturing actuator is configured to be detached from the stopper by retracting the puncturing actuator in a proximal direction along a longitudinal axis of the handle.

5. The apparatus according to claim 1, wherein the dilator comprises at least one of an inflatable balloon and a cautery device.

6. The apparatus according to claim 1, wherein the stopper is configured to fix a position of the puncturing actuator on the handle via frictional contact between the stopper and the handle.

7. The apparatus according to claim 1, wherein the handle further includes a catheter actuator that is configured to be operated to move the catheter independently of the guide tube, and a stopper of the catheter actuator that is separate from the catheter actuator and is configured to move along the handle independently of the catheter actuator.

8. The apparatus according to claim 7, wherein the handle further includes an apparatus actuator that is configured to be operated to simultaneously move the catheter and the guide tube, and a stopper of the apparatus actuator that is separate from the apparatus actuator and is configured to move along the handle independently of the apparatus actuator.

9. The apparatus according to claim 1, wherein the handle further includes an apparatus actuator that is configured to be operated to simultaneously move the catheter and the guide tube, and a stopper of the apparatus actuator that is separate from the apparatus actuator and is configured to move along the handle independently of the apparatus actuator.

10. The apparatus according to claim 1, wherein the handle further includes a connector at a distal end portion of the handle, the connector being configured to connect the handle to the endoscope.

* * * * *